United States Patent
Nakaie et al.

(10) Patent No.: US 10,193,075 B2
(45) Date of Patent: Jan. 29, 2019

(54) ANILINE DERIVATIVE AND USE THEREOF

(71) Applicant: NISSAN CHEMICAL INDUSTRIES, LTD., Tokyo (JP)

(72) Inventors: Naoki Nakaie, Funabashi (JP); Taichi Nakazawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/125,835

(22) PCT Filed: Mar. 11, 2015

(86) PCT No.: PCT/JP2015/057135
§ 371 (c)(1),
(2) Date: Sep. 13, 2016

(87) PCT Pub. No.: WO2015/137391
PCT Pub. Date: Sep. 17, 2015

(65) Prior Publication Data
US 2017/0005271 A1    Jan. 5, 2017

(30) Foreign Application Priority Data

Mar. 14, 2014    (JP) ................................ 2014-051978

(51) Int. Cl.
*H01L 51/00* (2006.01)
*C07C 209/10* (2006.01)
*C07C 211/54* (2006.01)
*C09D 5/24* (2006.01)
*H01L 51/50* (2006.01)

(52) U.S. Cl.
CPC ........ *H01L 51/0059* (2013.01); *C07C 209/10* (2013.01); *C07C 211/54* (2013.01); *C09D 5/24* (2013.01); *H01L 51/0003* (2013.01); *H01L 51/0081* (2013.01); *H01L 51/0085* (2013.01); *H01L 51/506* (2013.01); *H01L 51/5088* (2013.01)

(58) Field of Classification Search
CPC .......................... H01L 51/0059; C07C 209/01
See application file for complete search history.

(56) References Cited

U.S. PATENT DOCUMENTS

| 7,166,010 | B2 * | 1/2007 | Lamansky | H01L 51/5036 445/24 |
| 2004/0004433 | A1 | 1/2004 | Lamansky et al. | |
| 2008/0029742 | A1 | 2/2008 | Yoshimoto et al. | |
| 2009/0239045 | A1 | 9/2009 | Kato et al. | |
| 2010/0145067 | A1 | 6/2010 | Yokota et al. | |
| 2010/0159279 | A1 | 6/2010 | Kato et al. | |
| 2010/0230639 | A1 * | 9/2010 | Yamada | C07C 211/54 252/500 |

FOREIGN PATENT DOCUMENTS

| CN | 101331625 | A |   | 12/2008 |   |
| EP | 1748681 |   | * | 1/2007 | ........... C07C 211/54 |
| EP | 1748681 | A1 |   | 1/2007 |   |
| JP | 10-284252 | A |   | 10/1998 |   |
| JP | 10-2584252 |   | * | 10/1998 |   |
| JP | 2005-531915 | A |   | 10/2005 |   |
| JP | 2007-182401 | A |   | 7/2007 |   |
| JP | 2007182401 |   | * | 7/2007 |   |
| JP | 2008-127290 | A |   | 6/2008 |   |
| JP | 2008127290 |   | * | 6/2008 |   |
| WO | WO 2006/025342 | A1 |   | 3/2006 |   |
| WO | WO 2008/032616 | A1 |   | 3/2008 |   |
| WO | WO 2008/129947 | A1 |   | 10/2008 |   |
| WO | WO 2010/058777 | A1 |   | 5/2010 |   |

OTHER PUBLICATIONS

Louie et al., J.Am.Chem.Soc. (1997), 119, pp. 11695-11696.*
International Search Report (PCT/ISA/210) issued in PCT/JP2015/057135, dated May 26, 2015.
Written Opinion (PCT/ISA/237) issued PCT/JP2015/057135, dated May 26, 2015.
Extended European Search Report for European Application No. 15761044.5, dated Oct. 5, 2017.
Louie et al., "Discrete High Molecular Weight Triarylamine Dendrimers Prepared by Palladium-Catalyzed Amination," J. Am. Chem. Soc., vol. 119, No. 48, Jan. 1, 1997, pp. 11695-11696.
Chinese Office Action and Search Report for Chinese Application No. 201580013956.8, dated Nov. 3, 2017.

* cited by examiner

*Primary Examiner* — Paul V Ward
(74) *Attorney, Agent, or Firm* — Birch, Stewart, Kolasch & Birch, LLP

(57) ABSTRACT

Aniline derivatives such as are represented by, e.g., the formula have excellent solubility in organic solvents and make it possible to obtain an organic EL element having exceptional brightness characteristics when a thin film containing these derivatives as a charge transport material is applied to a hole injection layer.

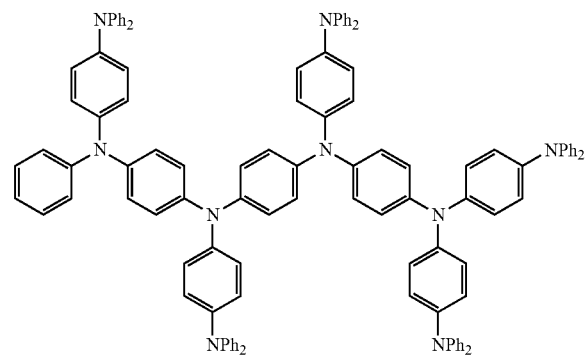

16 Claims, 1 Drawing Sheet

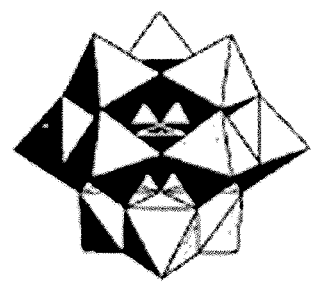
(A1)
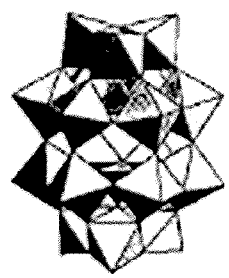
(A2)

ANILINE DERIVATIVE AND USE THEREOF

TECHNICAL FIELD

This invention relates to an aniline derivative and to the use thereof.

BACKGROUND ART

Charge-transporting thin-films made of organic compounds are used as emissive layers and charge injection layers in organic electroluminescence (EL) devices. In particular, a hole injection layer is responsible for transferring charge between an anode and a hole-transporting layer or an emissive layer, and thus serves an important function in achieving low-voltage driving and high brightness in organic EL devices.

Processes for forming the hole injection layer are broadly divided into dry processes such as vapor deposition and wet processes such as spin coating. Comparing these different processes, wet processes are better able to efficiently produce thin-films having a high flatness over a large area. Hence, with the progress currently underway toward larger-area organic EL displays, there exists a desire for hole injection layers that can be formed by wet processes.

In view of these circumstances, the inventors have developed charge-transporting materials which can be employed in various wet processes and which, when used in hole injection layers for organic EL devices, are capable of achieving excellent EL device characteristics. The inventors have also developed compounds of good solubility in organic solvents for use in such charge-transporting materials (see, for example, Patent Documents 1 to 4).

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

It is therefore an object of this invention to provide an aniline derivative which, as with the art disclosed in the above patent publications, exhibits good solubility in organic solvents and, when formed into a thin-film and used as a hole injection layer, enables an organic EL device endowed with excellent brightness characteristics to be achieved.

Means for Solving the Problems

The inventors have conducted extensive investigations, as a result of which they have discovered that specific aniline derivatives unable to assume a quinonediimine structure have an excellent solubility in organic solvents and that thin-films exhibiting high charge transportability can be obtained from varnishes prepared by dissolving such aniline derivatives in an organic solvent. The inventors have also found that when such a thin-film is used as a hole injection layer in an organic EL device, a device having a high brightness can be obtained.

Accordingly, the invention provides:
1. An aniline derivative characterized by having formula (1)

[Chemical Formula 1]

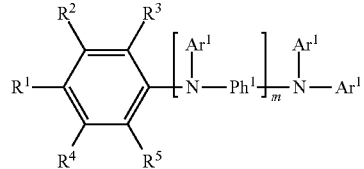

(1)

wherein $R^1$ to $R^5$ are each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom; each $Ph^1$ is independently a group of formula (P1)

[Chemical Formula 2]

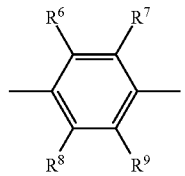

(P1)

($R^6$ to $R^9$ being each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom);

each $Ar^1$ is independently a group having any of formulas (A1) to (A14);

[Chemical Formula 3]

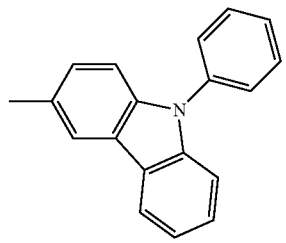

(A1)

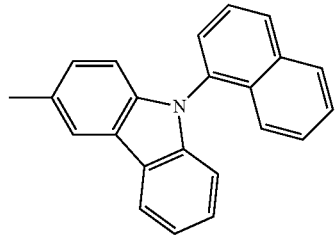

(A2)

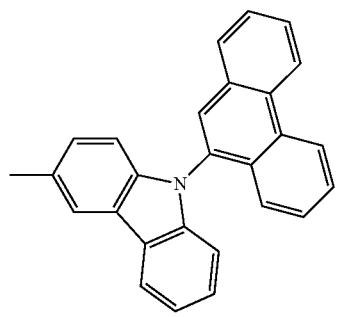
(A3)
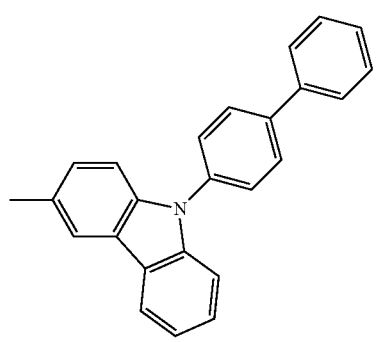
(A4)
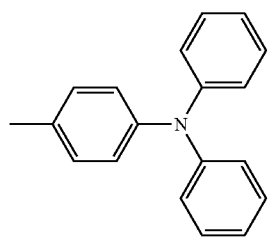
(A5)
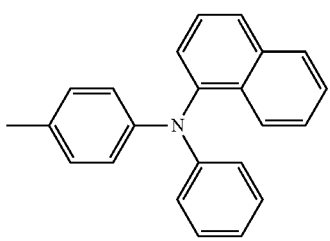
(A6)
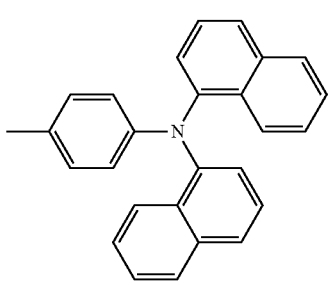
(A7)
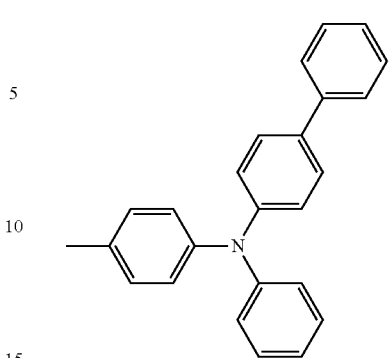
(A8)
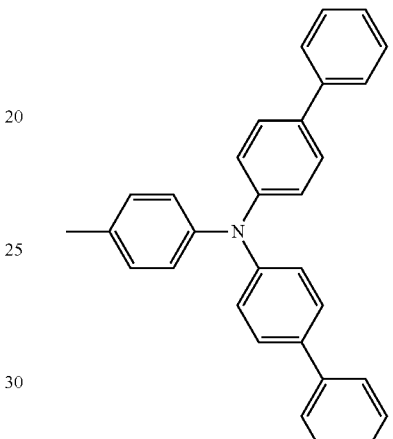
(A9)
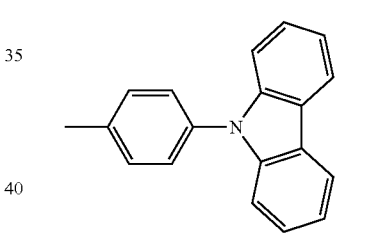
(A10)
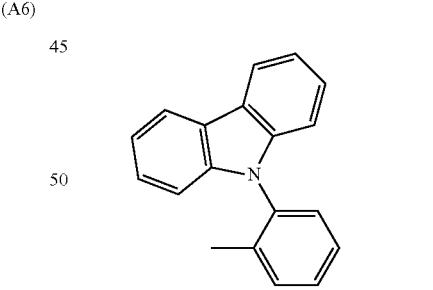
(A11)
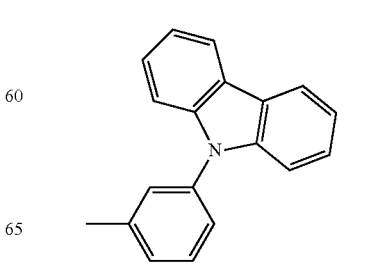
(A12)

-continued

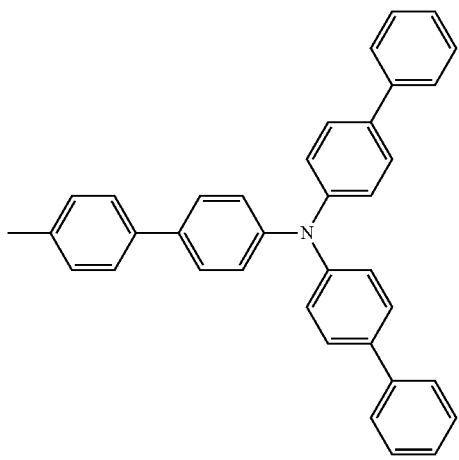

(A13)

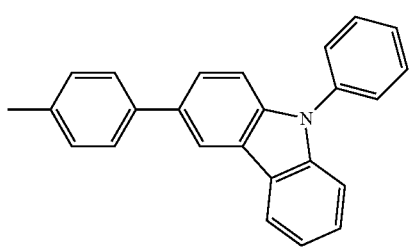

(A14)

and m is an integer from 1 to 5;
2. The aniline derivative of 1 above, wherein $R^1$ to $R^9$ are all hydrogen atoms;
3. The aniline derivative of 1 or 2 above, wherein each $Ar^1$ is independently a group having any of formulas (A1) to (A12);
4. The aniline derivative of 3 above, wherein each $Ar^1$ is independently a group having any of formulas (A1) to (A3), (A5) to (A7) and (A10) to (A12);
5. The aniline derivative of any one of 1 to 4 above, wherein the $Ar^1$ moieties are all identical groups;
6. A charge-transporting substance consisting of the aniline derivative of any one of 1 to 5 above;
7. A charge-transporting material comprising the charge-transporting substance of 6 above;
8. A charge-transporting varnish comprising the charge-transporting substance of 6 above and an organic solvent;
9. The charge-transporting varnish of 8 above which further comprises a dopant substance;
10. The charge-transporting varnish of 9 above, wherein the dopant substance comprises a halotetracyanoquinodimethane compound;
11. The charge-transporting varnish of 10 above, wherein the dopant substance further comprises a heteropolyacid;
12. A charge-transporting thin-film produced using the charge-transporting varnish of any one of 8 to 11 above;
13. An electronic device comprising the charge-transporting thin-film of 12 above;
14. An organic electroluminescent device comprising the charge-transporting thin-film of 12 above;
15. A method of producing a charge-transporting thin-film, which method is characterized by comprising the step of coating a substrate with the charge-transporting varnish of any one of 8 to 11 above and evaporating off the solvent; and
16. A method of preparing the aniline derivative of 1 above, which method is characterized by comprising the step of reacting an amine compound of formula (2)

[Chemical Formula 4]

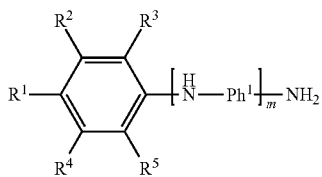

(2)

(wherein $R^1$ to $R^5$, $Ph^1$ and m are as defined above) with an aryl compound of formula (3)

[Chemical Formula 5]

$$Ar^1-Z \qquad (3)$$

(wherein Z is a halogen atom or a pseudo-halogen group, and $Ar^1$ is as defined above) in the presence of a catalyst.

Advantageous Effects of the Invention

The aniline derivative of the invention is readily soluble in organic solvents. A charge-transporting varnish can easily be prepared by dissolving the aniline derivative together with a dopant in an organic solvent.

Thin-films produced from the charge-transporting varnish of the invention exhibit high charge-transporting properties, and can thus be advantageously used as thin-films for organic EL devices and other electronic devices. In particular, by employing such a thin-film as a hole injection layer in an organic EL device, an organic EL device having excellent brightness characteristics can be obtained.

Also, the charge-transporting varnish of the invention can reproducibly produce thin-films of excellent charge transportability even using various wet processes capable of film formation over a large area, such as spin coating or slit coating, and is thus capable of fully accommodating recent advances in the field of organic EL devices.

BRIEF DESCRIPTION OF THE DRAWINGS

FIG. 1(A1) illustrates the formula of a polyacid having a Keggin-type chemical structure in which a heteroatom is positioned at the center of the molecule.

FIG. 1(A2) illustrates the formula of a polyacid having a Dawson-type chemical structure in which a heteroatom is positioned at the center of the molecule.

EMBODIMENT FOR CARRYING OUT THE INVENTION

The invention is described more fully below.
The aniline derivative according to this invention has formula (1).

[Chemical Formula 6]

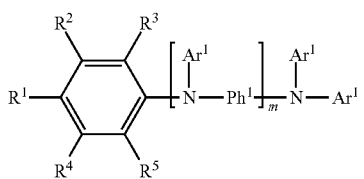

(1)

In the formula, each Ph¹ is independently a group of formula (P1).

[Chemical Formula 7]

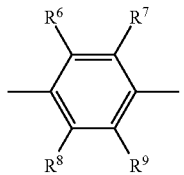

(P1)

$R^1$ to $R^9$ above are each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom.

Specific examples of halogen atoms include fluorine, chlorine, bromine and iodine atoms.

The alkyl group of 1 to 20 carbon atoms may be linear, branched or cyclic, and is exemplified by linear or branched alkyl groups of 1 to 20 carbon atoms such as methyl, ethyl, n-propyl, isopropyl, n-butyl, isobutyl, s-butyl, t-butyl, n-pentyl, n-hexyl, n-heptyl, n-octyl, n-nonyl and n-decyl groups; and cyclic alkyl groups of 3 to 20 carbon atoms such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

Specific examples of alkenyl groups of 2 to 20 carbon atoms include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pententyl, n-1-decenyl and n-1-eicosenyl groups.

Specific examples of alkynyl groups of 2 to 20 carbon atoms include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Specific examples of aryl groups of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Specific examples of heteroaryl groups of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

Of these, $R^1$ to $R^9$ are preferably hydrogen atoms, fluorine atoms, cyano groups, alkyl groups of 1 to 20 carbon atoms which may be substituted with halogen atoms, aryl groups of 6 to 20 carbon atoms which may be substituted with halogen atoms, or heteroaryl groups of 2 to 20 carbon atoms which may be substituted with halogen atoms; more preferably hydrogen atoms, fluorine atoms, cyano groups, alkyl groups of 1 to 10 carbon atoms which may be substituted with halogen atoms, or phenyl groups which may be substituted with halogen atoms; even more preferably hydrogen atoms or fluorine atoms; and most preferably hydrogen atoms.

Each $Ar^1$ in formula (1) above is independently a group having any of formulas (A1) to (A14).

Of these, from the standpoint of the solubility of the compound in organic solvents and to enhance the charge-transporting properties of the resulting thin-film, a group having any of formulas (A1) to (A12) is preferred, a group having any of formulas (A1) to (A3), (A5) to (A7) and (A10) to (A12) is more preferred, a group having any of formulas (A1), (A5) and (A10) to (A12) is even more preferred, and a group having formula (A1) or (A5) is still more preferred.

[Chemical Formula 8]

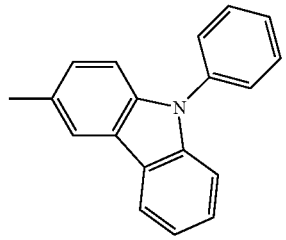

(A1)

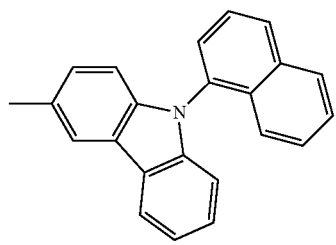

(A2)

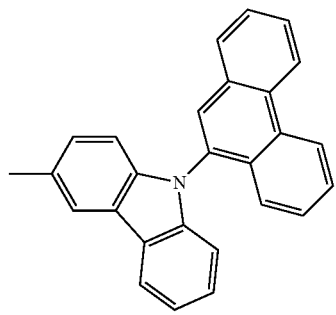

(A3)

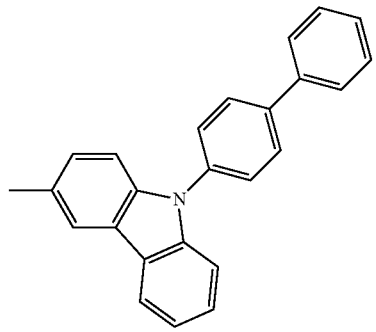

(A4)

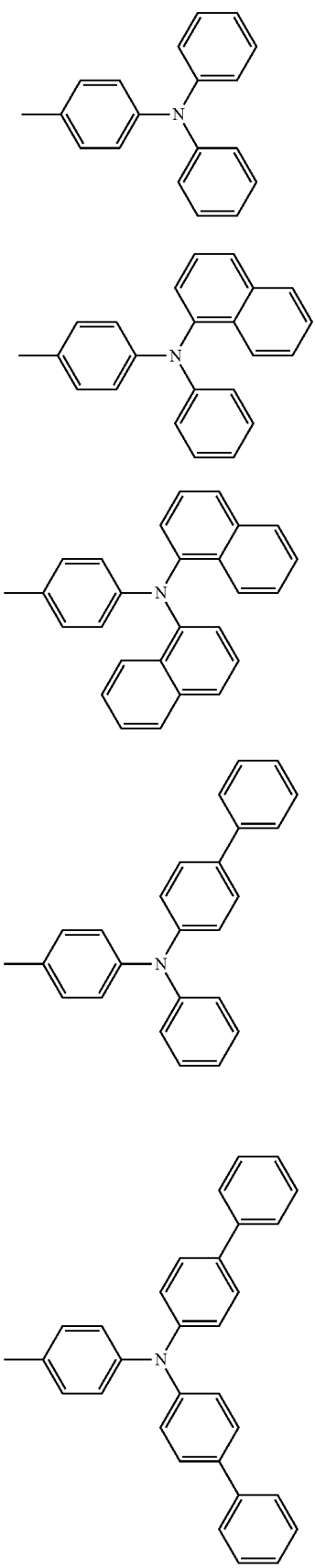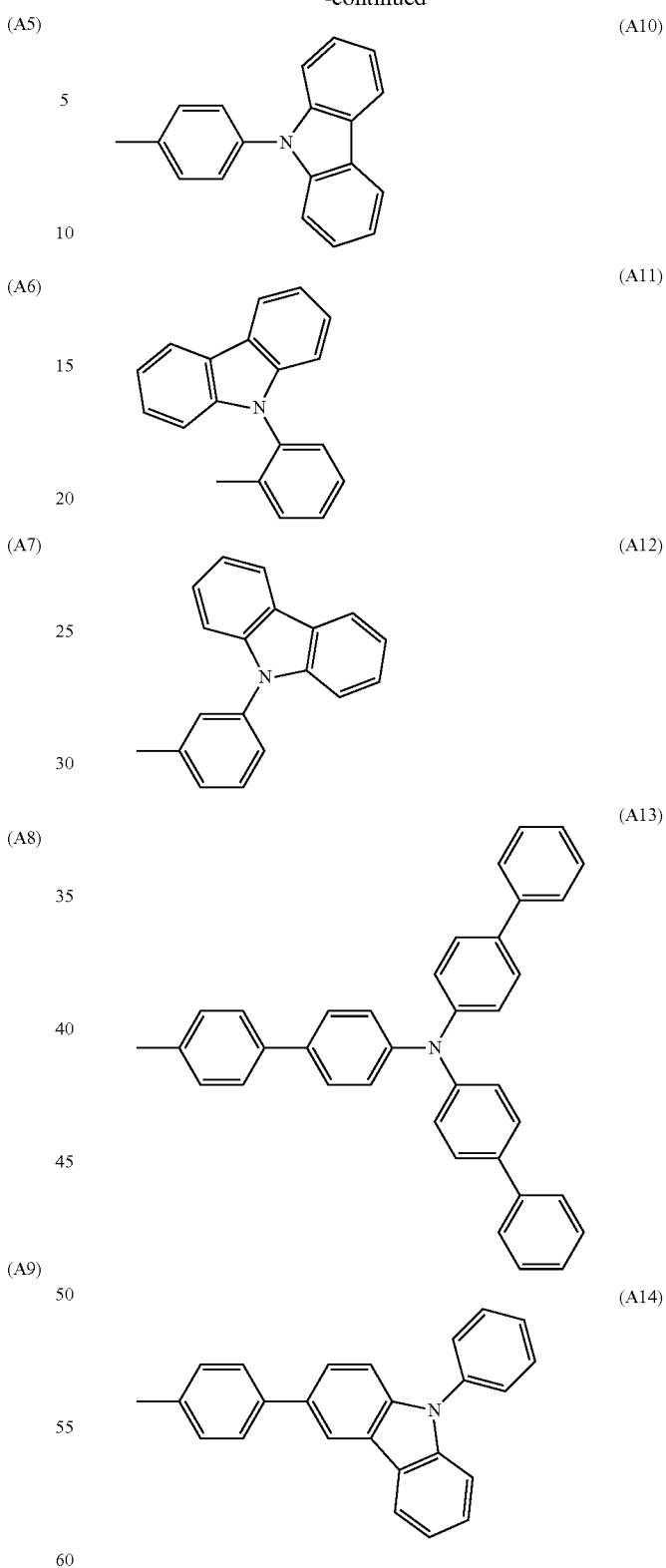
In formula (1), m is an integer from 1 to 5. From the standpoint of increasing the solubility of the compound in organic solvents, m is preferably 4 or less, and more preferably 3 or less. From the standpoint of increasing the charge transportability, m is preferably 2 or more, and more preferably 3 or more.

In this invention, the number of carbon atoms on the above alkyl, alkenyl and alkynyl groups is preferably 10 or less, more preferably 6 or less, and even more preferably 4 or less.

The number of carbon atoms on the aryl groups and heteroaryl groups is preferably 14 or less, more preferably 10 or less, and even more preferably 6 or less.

In formula (1), all $Ar^1$ groups are preferably identical groups, and all $Ph^1$ groups are preferably identical groups.

The inventive aniline derivative of formula (1) can be prepared by reacting an amine compound of formula (2) with an aryl compound of formula (3) in the presence of a catalyst.

[Chemical Formula 9]

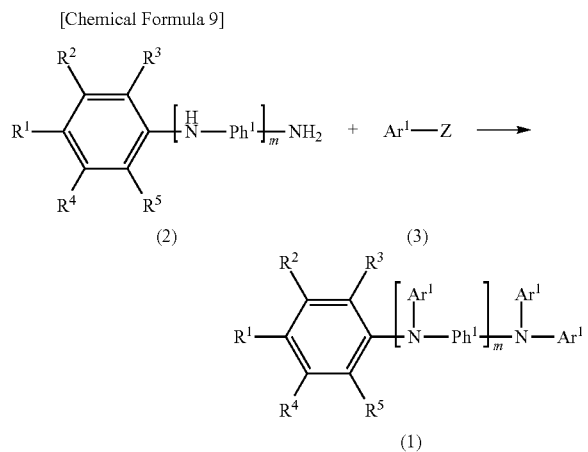

Here, Z is a halogen atom or a pseudo-halogen group, and $R^1$ to $R^5$, $Ar^1$, $Ph^1$ and m are as defined above.

The halogen atom is exemplified in the same way as above.

The pseudo-halogen group is exemplified by (fluoro)alkylsulfonyloxy groups such as methanesulfonyloxy, trifluoromethanesulfonyloxy and nanofluorobutanesulfonyloxy groups; and aromatic sulfonyloxy groups such as benzenesulfonyloxy and toluenesulfonyloxy groups.

The charging ratio between the amine compound of formula (2) and the aryl compound of formula (3) may be set so as to make the amount of the aryl compound at least 1 equivalent, and preferably about 1 to 1.2 equivalents, with respect to the molar amount of all NH groups on the amine compound.

The catalyst used in the reaction is exemplified by copper catalysts such as copper chloride, copper bromide and copper iodide; and palladium catalysts such as tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$) and bis(tri(t-butylphosphine)palladium ($Pd(P-t-Bu_3)_2$). These catalysts may be used singly, or two or more may be used in combination. Also, these catalysts may be used together with suitable known ligands.

The amount of catalyst used may be set to about 0.2 mole per mole of the aryl compound of formula (3), with about 0.15 mole being preferred.

When ligands are used, the amount thereof may be set to from 0.1 to 5 equivalents, and preferably from 1 to 2 equivalents, with respect to the metal catalyst used.

Each of the above reactions may be carried out in a solvent. When a solvent is used, the type of solvent is not particularly limited, provided it does not have an adverse effect on the reaction. Illustrative examples include aliphatic hydrocarbons (pentane, n-hexane, n-octane, n-decane, decalin, etc.), halogenated aliphatic hydrocarbons (chloroform, dichloromethane, dichloroethane, carbon tetrachloride, etc.), aromatic hydrocarbons (benzene, nitrobenzene, toluene, o-xylene, m-xylene, p-xylene, mesitylene, etc.), halogenated aromatic hydrocarbons (chlorobenzene, bromobenzene, o-dichlorobenzene, m-dichlorobenzene, p-dichlorobenzene, etc.), ethers (diethyl ether, diisopropyl ether, t-butyl methyl ether, tetrahydrofuran, dioxane, 1,2-dimethoxyethane, 1.2-diethoxyethane, etc.), ketones (acetone, methyl ethyl ketone, methyl isobutyl ketone, di-n-butyl ketone, cyclohexanone, etc.), amides (N,N-dimethylformamide, N,N-dimethylacetamide, etc.), lactams and lactones (N-methylpyrrolidone, γ-butyrolactone, etc.), ureas (N,N-dimethylimidazolidinone, tetramethylurea, etc.), sulfoxides (dimethylsulfoxide, sulfolane, etc.), and nitriles (acetonitrile, propionitrile, butyronitrile, etc.). These solvents may be used singly, or two or more may be used in admixture.

The reaction temperature may be suitably set in the range of the melting point to the boiling point of the solvent used, with a temperature of about 0 to 200° C. being preferred, and a temperature of 20 to 150° C. being more preferred.

Following reaction completion, the target aniline derivative can be obtained by work-up in the usual manner.

Illustrative, non-limiting, examples of the aniline derivative of formula (1) are shown below.

[Chemical Formula 10]

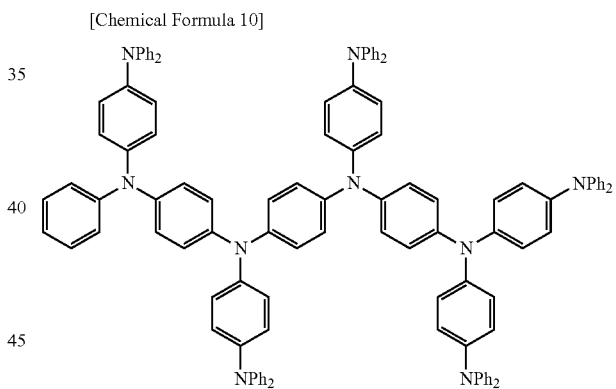

The charge-transporting varnish of the invention includes a charge-transforming substance consisting of the aniline derivative of formula (1), and an organic solvent. Depending on the intended use of the resulting thin-film, the varnish may include a dopant substance for the purpose of, for example, enhancing the charge transportability.

The dopant substance is not particularly limited, provided it dissolves in at least one of the solvents used in the varnish. Use can be made of either an inorganic dopant substance or an organic dopant substance.

Heteropolyacids are especially preferred as inorganic dopant substances.

"Heteropolyacid" refers to a polyacid having a structure in which a heteroatom is positioned at the center of the molecule—typically the Keggin-type chemical structure shown in the formula of FIG. 1(A1) or the Dawson-type chemical structure shown in the formula of FIG. 1(A2) and which is obtained by the condensation of an isopolyacid that is an oxoacid of vanadium (V), molybdenum (Mo), tungsten (W) or the like with an oxoacid of a different element. Examples of such oxoacids of a different element include primarily oxoacids of silicon (Si), phosphorus (P) and arsenic (As).

Examples of heteropolyacids include phosphomolybdic acid, silicomolybdic acid, phosphotungstic acid, silicotungstic acid and phosphotungstomolybdic acid. These may be used singly, or two or more may be used in combination. The heteropolyacid compound used in this invention may be acquired as a commercial product or may be synthesized by a known method.

In particular, when one heteropolyacid is used, this one heteropolyacid is preferably phosphotungstic acid or phosphomolybdic acid, and most preferably phosphotungstic acid. When two or more heteropolyacids are used, one of the two or more heteropolyacids is preferably phosphotungstic acid or phosphomolybdic acid, and more preferably phosphotungstic acid.

Even a heteropolyacid having, in quantitative analysis such as elemental analysis, numbers for the elements which are higher or lower than in the structure indicated by the general formula may be used in this invention, provided it was acquired as a commercial product or was suitably synthesized according to a known method of synthesis.

For example, phosphotungstic acid is generally represented by the chemical formula $H_3(PW_{12}O_{40}) \cdot nH_2O$ and phosphomolybdic acid is generally represented by the chemical formula $H_3(PMo_{12}O_{40}) \cdot nH_2O$. In quantitative analysis, regardless of whether the numbers for the elements P (phosphorus), O (oxygen) and W (tungsten) or Mo (molybdenum) within these formulas are high or low, so long as the heteropolyacid was acquired as a commercial product or suitably synthesized by a known method of synthesis, it may be used in this invention. In such cases, the weight of the heteropolyacid specified in this invention refers not to the weight of pure phosphotungstic acid within the product of synthesis or the commercial product (phosphotungstic acid content), but rather, in the form that is available as a commercial product or the form that can be isolated by a known method of synthesis, to the total weight in a state that includes water of hydration and other impurities.

The amount of heteropolyacid included in the charge-transporting varnish of the invention, expressed as a ratio of weight relative to unity (1) for the charge-transporting substance consisting of the aniline derivative of the invention, is generally about 0.01 to 50, preferably about 0.1 to 10, and more preferably about 1.0 to 5.0.

Tetracyanoquinodimethane derivatives and benzoquinone derivatives are especially preferred as organic dopant substances.

Specific examples of tetracyanoquinodimethane derivatives include 7,7,8,8-tetracyanoquinodimethane (TCNQ) and halotetracyanoquinodimethanes of formula (4).

Specific examples of benzoquinone derivatives include tetrafluoro-1,4-benzoquinone (F4BQ), tetrachloro-1,4-benzoquinone (chloranil), tetrabromo-1,4-benzoquinone and 2,3-dichloro-5,6-dicyano-1,4-benzoquinone (DDQ).

[Chemical Formula 12]

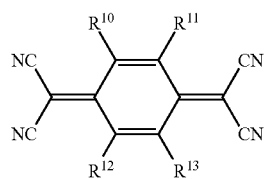

(4)

In the formula, $R^{10}$ to $R^{13}$ are each independently a hydrogen atom or a halogen atom, with at least one being a halogen atom, preferably at least two being halogen atoms, more preferably at least three being halogen atoms, and most preferably all four being halogen atoms.

The halogen atoms are exemplified in the same way as above, although they are preferably fluorine atoms or chlorine atoms, and more preferably fluorine atoms.

Illustrative examples of halotetracyanoquinodimethane compounds include 2-fluoro-7,7,8,8-tetracyanoquinodimethane, 2-chloro-7,7,8,8-tetracyanoquinodimethane, 2,5-difluoro-7,7,8,8-tetracyanoquinodimethane, 2,5-dichloro-7,7,8,8-tetracyanoquinodimethane, 2,3,5,6-tetrachloro-7,7,8,8-tetracyanoquinodimethane and 2,3,5,6-tetrafluoro-7,7,8,8-tetracyanoquinodimethane (F4TCNQ). In this invention, F4TCNQ is most preferred.

The content of tetracyanoquinodimethane derivative and benzoquinone derivative in the charge-transporting varnish of the invention is preferably from 0.0001 to 50 equivalents, more preferably from 0.001 to 20 equivalents, and even more preferably from 0.01 to 10 equivalents, with respect to the aniline derivative of the invention.

In this invention, based on such considerations as reproducibly obtaining a thin-film of high charge transportability and the availability of the dopant substance, it is preferable to include at least one halotetracyanoquinodimethane and/or benzoquinone derivative, and more preferable to include F4TCNQ and/or DDQ.

When the resulting thin-film is to be used as a hole injection layer in an organic EL device, based on such considerations as reproducibly obtaining devices having a good longevity and the availability of the dopant substance, it is preferable to include as the dopant substance at least one halotetracyanoquinodimethane and/or benzoquinone derivative, and also a heteropolyacid; more preferable to include at least one halotetracyanoquinodimethane and/or benzoquinone derivative, and also phosphotungstic acid and/or phosphomolybdic acid; and even more preferable to include F4TCNQ and/or DDQ, and also phosphotungstic acid.

In addition, when the resulting thin-film is to be used as a hole injection layer in an organic EL device, to reproducibly obtain devices having a good longevity, it is preferable for the charge-transporting varnish of the invention to include an organosilane compound.

The organosilane compound is exemplified by dialkoxysilane compounds, trialkoxysilane compounds and tetraalkoxysilane compounds. These may be used singly, or two or more may be used in combination.

In particular, the organosilane compound is preferably a dialkoxysilane compound or a trialkoxysilane compound, and more preferably a trialkoxysilane compound.

These alkoxysilane compounds are exemplified by compounds of formulas (5) to (7).

  (5)

  (6)

  (7)

In these formulas, each R is independently an alkyl group of 1 to 20 carbon atoms which may be substituted with an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, or a heteroaryl group of 2 to 20 carbon atoms which may be substituted with $Z^2$. Each R' is independently an alkyl group of 1 to 20 carbon atoms which may be substituted with $Z^3$, an alkenyl group of 2 to 20 carbon atoms which may be substituted with $Z^3$, an alkynyl group of 2 to 20 carbon atoms which may be substituted with $Z^3$, an aryl group of 6 to 20 carbon atoms which may be substituted with $Z^4$, or a heteroaryl group of 2 to 20 carbon atoms which may be substituted with $Z^4$.

$Z^1$ is a halogen atom, an aryl group of 6 to 20 carbon atoms which may be substituted with $Z^5$, or a heteroaryl group of 2 to 20 carbon atoms which may be substituted with $Z^5$. $Z^2$ is a halogen atom, an alkyl group of 1 to 20 carbon atoms which may be substituted with $Z^5$, an alkenyl group of 2 to 20 carbon atoms which may be substituted with $Z^5$, or an alkynyl group of 2 to 20 carbon atoms which may be substituted with $Z^5$.

$Z^3$ is a halogen atom, an aryl group of 6 to 20 carbon atoms which may be substituted with $Z^5$, a heteroaryl group of 2 to 20 carbon atoms which may be substituted with $Z^5$, an epoxycyclohexyl group, a glycidoxy group, a methacryloxy group, an acryloxy group, a ureido group (—NHCONH$_2$), a thiol group, an isocyanate group (—NCO), an amino group, a —NHY$^1$ group, or a —NY$^2$Y$^3$ group. $Z^4$ is a halogen atom, an alkyl group of 1 to 20 carbon atoms which may be substituted with $Z^5$, an alkenyl group of 2 to 20 carbon atoms which may be substituted with $Z^5$, an alkynyl group of 2 to 20 carbon atoms which may be substituted with $Z^5$, an epoxycyclohexyl group, a glycidoxy group, a methacryloxy group, an acryloxy group, a ureido group (—NHCONH$_2$), a thiol group, an isocyanate group (—NCO), an amino group, a —NHY$^1$ group or a —NY$^2$Y$^3$ group, with Y$^1$ to Y$^3$ each being independently an alkyl group of 1 to 20 carbon atoms which may be substituted with $Z^5$, an alkenyl group of 2 to 20 carbon atoms which may be substituted with $Z^5$, an alkynyl group of 2 to 20 carbon atoms which may be substituted with $Z^5$, an aryl group of 6 to 20 carbon atoms which may be substituted with $Z^5$, or a heteroaryl group of 2 to 20 carbon atoms which may be substituted with $Z^5$.

$Z^5$ is a halogen atom, an amino group, a nitro group, a cyano group or a thiol group.

In formulas (5) to (7), the halogen atom, alkyl group of 1 to 20 carbon atoms, alkenyl group of 2 to 20 carbon atoms, alkynyl group of 2 to 20 carbon atoms, aryl group of 6 to 20 carbon atoms and heteroaryl group of 2 to 20 carbon atoms are exemplified in the same way as above.

In R and R', the number of carbon atoms on the alkyl, alkenyl and alkynyl groups is preferably 10 or less, more preferably 6 or less, and even more preferably 4 or less.

Also, the number of carbon atoms on the aryl and heteroaryl groups is preferably 14 or less, more preferably 10 or less, and even more preferably 6 or less.

R is preferably an alkyl group of 1 to 20 carbon atoms or alkenyl group of 2 to 20 carbon atoms which may be substituted with $Z^1$, or an aryl group of 6 to 20 carbon atoms which may be substituted with $Z^2$; more preferably an alkyl group of 1 to 6 carbon atoms or alkenyl group of 2 to 6 carbon atoms which may be substituted with $Z^1$, or a phenyl group which may be substituted with $Z^2$; even more preferably an alkyl group of 1 to 4 carbon atoms which may be substituted with $Z^1$ or a phenyl group which may be substituted with $Z^2$; and still more preferably a methyl group or ethyl group which may be substituted with $Z^1$.

R' is preferably an alkyl group of 1 to 20 carbon atoms which may be substituted with $Z^3$, or an aryl group of 6 to 20 carbon atoms which may be substituted with $Z^4$; more preferably an alkyl group of 1 to 10 carbon atoms which may be substituted with $Z^3$, or an aryl group of 6 to 14 carbon atoms which may be substituted with $Z^4$; even more preferably an alkyl group of 1 to 6 carbon atoms which may be substituted with $Z^3$, or an aryl group of 6 to 10 carbon atoms which may be substituted with $Z^4$; and still more preferably an alkyl group of 1 to 4 carbon atoms which may be substituted with $Z^3$, or a phenyl group which may be substituted with $Z^4$.

The plurality of R moieties may all be the same or different, and the plurality of R' moieties may likewise all be the same or different.

$Z^1$ is preferably a halogen atom or an aryl group of 6 to 20 carbon atoms which may be substituted with $Z^5$, more preferably a fluorine atom or a phenyl group which may be substituted with $Z^5$, and most preferably does not exist (i.e., is non-substituting).

$Z^2$ is preferably a halogen atom or an alkyl group of 1 to 20 carbon atoms which may be substituted with $Z^5$, more preferably a fluorine atom or an alkyl group of 1 to 10 carbon atoms which may be substituted with $Z^5$, and most preferably does not exist (i.e., is non-substituting).

$Z^3$ is preferably a halogen atom, a phenyl group which may be substituted with $Z^5$, a furanyl group which may be substituted with $Z^5$, an epoxycyclohexyl group, a glycidoxy group, a methacryloxy group, an acryloxy group, a ureido group, a thiol group, an isocyanate group, an amino group, a phenylamino group which may be substituted with $Z^5$, or a diphenylamino group which may be substituted with $Z^5$; more preferably a halogen atom; and even more preferably a fluorine atom or does not exist (i.e., is non-substituting).

$Z^4$ is preferably a halogen atom, an alkyl group of 1 to 20 carbon atoms which may be substituted with $Z^5$, a furanyl group which may be substituted with $Z^5$, an epoxycyclohexyl group, a glycidoxy group, a methacryloxy group, an acryloxy group, a ureido group, a thiol group, an isocyanate group, an amino group, a phenylamino group which may be substituted with $Z^5$, or a diphenylamino group which may be substituted with $Z^5$; more preferably a halogen atom; and even more preferably a fluorine atom or does not exist (i.e., is non-substituting).

$Z^5$ is preferably a halogen atom, and more preferably a fluorine atom or does not exist (i.e., is non-substituting).

Examples of organosilane compounds that may be used in this invention include, but are not limited to, the following.

Specific examples of dialkoxysilane compounds include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 3-mercaptopropylmethyldimethoxysilane, γ-aminopropylmethyldiethoxysilane, N-(2-aminoethyl)aminopropylmethyldimethoxysilane and 3,3,3-trifluoropropylmethyldimethoxysilane.

Specific examples of trialkoxysilane compounds include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, octadecyltrimethoxysilane, octadecyltriethoxysilane, phenyltrimethoxysilane, phenyltriethoxysilane, vinyltrimethoxysilane, vinyltriethoxysilane, 3-aminopropyltrimethoxysilane, 3-aminopropyltriethoxysilane, 3-glycidoxypropyltrimethoxysilane, 3-glycidoxypropyltriethoxysilane, 3-methacryloxypropyltrimethoxysilane, 3-methacryloxypropyltriethoxysilane, triethoxy(4-(trifluoromethyl)phenyl)silane, dodecyltriethoxysilane, 3,3,3-trifluoropropyltrimethoxysilane, to (triethoxysilyl)cyclohexane, perfluorooctylethyltriethoxysilane, triethoxyfluorosilane, tridecafluoro-1,1,2,2-tetrahydrooctyltriethoxysilane, pentafluorophenyltrimethoxysilane, pentafluorophenyltriethoxysilane, 3-(heptafluoroisopropoxy)propyltriethoxysilane, heptadecafluoro-1,1,2,2-tetrahydrodecyltriethoxysilane, triethoxy-2-thienylsilane and 3-(triethoxysilyl)furan.

Specific examples of tetraalkoxysilane compounds include tetraethoxysilane, tetramethoxysilane and tetrapropoxysilane.

Of these, 3,3,3-trifluoropropylmethyldimethoxysilane, triethoxy(4-(trifluoromethyl)phenyl)silane, 3,3,3-trifluoropropyltrimethoxysilane, perfluorooctylethyltriethoxysilane, pentafluorophenyltrimethoxysilane and pentafluorophenyltriethoxysilane are preferred.

When the charge-transporting varnish of the invention includes an organosilane compound, the content of the organosilane compound, based on the total weight of the charge-transporting substance (or, in cases where a dopant substance is included, based on the total weight of the charging-transporting substance and the dopant substance), is generally about 0.1 to 50 weight %. However, to suppress a decrease in the charge transportability of the thin-film and also increase the ability to inject holes in a layer that is stacked so as to be in contact with the above-described hole injection layer on the cathode side, the content is preferably about 0.5 to 40 weight %, more preferably about 0.8 to 30 weight %, and even more preferably about 1 to 20 weight %.

In addition to a charge-transporting substance consisting of the above-described aniline derivative, the charge-transporting varnish of the invention may include also another charge-transporting substance that is known.

Highly solvating solvents which are capable of dissolving well the charge-transporting substance and the dopant substance may be used as the organic solvent employed when preparing the charge-transporting varnish.

Examples of such highly solvating solvents that may be used include, but are not limited to, organic solvents such as cyclohexanone, N,N-dimethylformamide, N,N-dimethylacetamide, N,N-dimethylisobutyramide, N-methylpyrrolidone, 1,3-dimethyl-2-imidazolidinone and diethylene glycol monomethyl ether. These solvents may be used singly, or two or more may be used in admixture. The amount thereof may be set to 5 to 100 weight %, based on the overall solvent used in the varnish.

The charge-transporting substance and dopant substance are preferably in a state where both are either completely dissolved or uniformly dispersed in the solvent; and are more preferably completely dissolved.

In the practice of the invention, by including in the varnish at least one high-viscosity organic solvent having a viscosity at 25° C. of 10 to 200 mPa·s, especially 35 to 150 mPa·s, and a boiling point at standard pressure (atmospheric pressure) of 50 to 300° C., especially 150 to 250° C., the viscosity of the varnish is easily adjusted, thus making it possible to prepare a varnish which reproducibly gives thin-films of high flatness and is suitable for the coating method to be used.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. These solvents may be used singly, or two or more may be used in admixture.

The amount of high-viscosity organic solvent added as a proportion of the overall solvent used in the varnish of the invention is preferably within a range where no precipitation of solids occurs. The amount of such addition is preferably 5 to 80 weight %, provided that no precipitation of solids occurs.

In addition, other solvents may be admixed in a proportion with respect to the overall solvent used in the varnish of 1 to 90 weight %, and preferably 1 to 50 weight %, for such purposes as to enhance the substrate wettability by the varnish, adjust the solvent surface tension, adjust the polarity, and adjust the boiling point.

Examples of such solvents include, but are not limited to, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly, or two or more may be used in admixture.

The viscosity of the inventive varnish is set as appropriate for the thickness and other properties of the thin-film to be produced and the solids concentration of the varnish, but is generally from 1 to 50 mPa·s at 25° C.

The solids concentration of the charge-transporting varnish of this invention is set as appropriate based on such considerations as the viscosity, surface tension and other properties of the varnish and the thickness and other properties of the thin-film to be produced, and is generally about 0.1 to 10.0 weight %. To improve the coating properties of the varnish, the solids concentration of the varnish is preferably about 0.5 to 5.0 weight %, and more preferably about 1.0 to 3.0 weight %.

Examples of methods for preparing the charge-transporting varnish include, but are not particularly limited to, the approach of dissolving the aniline derivative of the invention in a highly solvating solvent and then adding thereto a high-viscosity organic solvent, and the approach of mixing together a highly solvating solvent and a high-viscosity organic solvent and then dissolving therein the aniline derivative of the invention.

In this invention, from the standpoint of reproducibly obtaining a higher flatness thin-film, it is desirable for the charge-transporting varnish to be obtained by dissolving the charge-transporting substance, dopant substances, etc. in the organic solvent, then filtering the solution using a submicron-order filter or the like.

A charge-transporting thin-film can be formed on a substrate by coating the inventive charge-transporting varnish onto the substrate and baking.

Examples of the varnish coating method include, but are not particularly limited to, dipping, spin coating, transfer printing, roll coating, brush coating, inkjet printing, spraying and slit coating. The viscosity and surface tension of the varnish are preferably adjusted according to the coating method to be used.

When using the varnish of the invention, the baking atmosphere is not particularly limited. A thin-film having a uniform film surface and high charge transportability can be obtained not only in an open-air atmosphere, but even in an inert gas such as nitrogen or in a vacuum. However, to reproducibly obtain a thin-film having a high charge transportability, an open-air atmosphere is preferred.

The baking temperature is suitably set in the range of about 100 to 260° C. while taking into account such factors as the intended use of the resulting thin-film, the degree of charge transportability to be imparted to the thin-film, and the type and boiling point of the solvent. When the thin-film thus obtained is to be used as a hole injection layer in an organic EL device, the baking temperature is preferably about 140 to 250° C., and more preferably about 145 to 240° C.

During baking, a temperature change in two or more steps may be applied for such purposes as to achieve more uniform film formability or to induce the reaction to proceed on the substrate. Heating may be carried out using a suitable apparatus such as a hot plate or an oven.

The thickness of the charge-transporting thin-film is not particularly limited. However, when the thin-film is to be used as a hole injection layer in an organic EL device, a film thickness of 5 to 200 nm is preferred. Methods for changing the film thickness include, for example, changing the solids concentration in the varnish and changing the amount of solution on the substrate during coating.

The charge-transporting thin-film of the invention can be suitably used as a hole injection layer in an organic EL device, although use as charge-transporting functional layers such as a hole injecting and transporting layer is also possible.

The materials and method employed to fabricate organic light-emitting diode (OLED) devices using the charge-transporting varnish of the invention are exemplified by, but not limited to, those mentioned below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

A method of fabricating an OLED device having a hole injection layer made of a thin-film obtained from the charge-transporting varnish of the invention is described below by way of illustration.

A hole injection layer is formed on an electrode by coating the charge-transporting varnish of the invention onto an anode substrate and baking in the manner described above. The workpiece is then introduced into a vacuum deposition system, where a hole transport layer, emissive layer, electron transport layer, electron transport layer/hole-blocking layer and cathode metal are vapor-deposited in this order to form the OLED device. Where necessary, an electron-blocking layer may be provided between the emissive layer and the hole transport layer.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole transport layer-forming materials include triarylamines such as
(triphenylamine) dimer derivatives,
[(triphenylamine) dimer] spirodimer,
N,N'-bis(naphthalen-1-yl)-N,N'-bis(phenyl)benzidine (α-NPD),
N,N'-bis(naphthalen-2-yl)-N,N'-bis(phenyl)benzidine,
N,N'-bis(3-methylphenyl)-N,N'-bis(phenyl)benzidine,
N,N'-bis(3-methylphenyl)-N,N'-bis(phenyl)-9,9-spirobifluorene,
N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene,
N,N'-bis(naphthalen-1-yl)-N,N'-bis(phenyl)-9,9-diphenylfluorene,
N,N'-bis(naphthalen-1-yl)-N,N'-bis(phenyl)-2,2'-dimethylbenzidine,
2,2',7,7'-tetrakis(N,N-diphenylamino)-9,9-splrobifluorene,
9,9-bis[4-(N,N-bisbiphenyl-4-ylamino)phenyl]-9H-fluorene,
9,9-bis[4-(N,N-bisnaphthalen-2-ylamino)phenyl]-9H-fluorene,
9,9-bis[4-(N-naphthalen-1-yl-N-phenylamino)phenyl]-9H-fluorene,
2,2',7,7'-tetrakis[N-naphthalenyl(phenyl)amino]-9,9-spirobifluorene,
N,N'-bis(phenanthren-9-yl)-N,N'-bis(phenyl)benzidine,
2,2'-bis[N,N-bis(biphenyl-4-yl)amino]-9,9-spirobifluorene,
2,2'-bis(N,N-diphenylamino)-9,9-spirobifluorene,
di[4-(N,N-di(p-tolyl)amino)phenyl]cyclohexane,
2,2',7,7'-tetra(N,N-di(p-tolyl))amino-9,9-spirobifluorene,
N,N,N',N'-tetranaphthalen-2-ylbenzidine,
N,N,N',N'-tetra(3-methylphenyl)-3,3'-dimethylbenzidine,
N,N'-di(naphthalenyl)-N,N'-di(naphthalen-2-yl)benzidine,
N,N,N',N'-tetra(naphthalenyl)benzidine,
N,N'-di(naphthalen-2-yl)-N,N'-diphenylbenzidine-1-4-diamine,
$N^1,N^4$-diphenyl-$N^1,N^4$-di(m-tolyl)benzene-1,4-diamine,
$N^2,N^2,N^6,N^6$-tetraphenylnaphthalene-2,6-diamine,
tris(4-(quinolin-8-yl)phenyl)amine,
2,2'-bis(3-(N,N-di(p-tolyl)amino)phenyl)biphenyl,
4,4',4''-tris[3-methylphenyl(phenyl)amino]triphenylamine (m-MTDATA) and
4,4',4''-tris[1-naphthyl(phenyl)amino]triphenylamine (1-TNATA); and
oligothiophenes such as
5,5''-bis-{4-[bis(4-methylphenyl)amino]phenyl}-2,2':5',2''-terthiophene (BMA-3T).

Specific examples of emissive layer-forming materials include tris(8-quinolinolate) aluminum(III) (Alq$_3$), bis(8-quinolinolate) zinc(II) (Znq$_2$), bis(2-methyl-8-quinolinolate)-(p-phenylphenolate) aluminum(III) (BAlq),
4,4'-bis(2,2-diphenylvinyl)biphenyl,
9,10-di(naphthalen-2-yl)anthracene,
2-t-butyl-9,10-di(naphthalen-2-yl)anthracene, 2,7-bis[9,9-di(4-methylphenyl)fluoren-2-yl]-9,9-di(4-methylphenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)fluoren-2-yl]-9,9-di(4-methylphenyl)-fluorene,
2,2'-dipyrenyl-9,9-spirobifluorene,
1,3,5-tris(pyren-1-yl)benzene,
9,9-bis[4-(pyrenyl)phenyl]-9H-fluorene,
2,2'-bi(9,10-diphenylanthracene),
2,7-dipyrenyl-9,9-spirobifluorene, 1,4-di(pyren-1-yl)benzene,
1,3-di(pyren-1-yl)benzene, 6,13-di(biphenyl-4-yl)pentacene,
3,9-di(naphthalen-2-yl)perylene,
3,10-di(naphthalen-2-yl)perylene,
tris[4-(pyrenyl)phenyl]amine,
10,10'-di(biphenyl-4-yl)-9,9'-bianthracene,
N,N'-di(naphthalen-1-yl)-N,N'-diphenyl[1,1':4',1":4",1"'-quaterphenyl]-4,4"'-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)-pyrene,
1-(7-(9,9'-bianthracen-10-yl)-9,9-dihexyl-9H-fluoren-2-yl)-pyrene,
1,3-bis(carbazol-9-yl)benzene,
1,3,5-tris(carbazol-9-yl)benzene,
4,4',4"-tris(carbazol-9-yl)triphenylamine,
4,4'-bis(carbazol-9-yl)biphenyl (CBP),
4,4'-bis(carbazol-9-yl)-2,2'-dimethylbiphenyl,
2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene,
9,9-bis[4-(carbazol-9-yl)phenyl]fluorene,
2,7-bis(carbazol-9-yl)-9,9-spirobifluorene,
1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene,
4,4"-di(triphenylsilyl)-p-terphenyl,
4,4'-di(triphenylsilyl)biphenyl,
9-(4-t-butylphenyl)-3,6-bis(triphenylsilyl)-9H-carbazole,
9-(4-t-butylphenyl)-3,6-ditrityl-9H-carbazole,
9-(4-t-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yldiphenylphosphine oxide,
9,9'-(5-triphenylsilyl)-1,3-phenylene)bis(9H-carbazole),
3-(2,7-bis(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]pyrene,
4,7-di(9H-carbazol-9-yl)-1,10-phenanthroline,
2,2'-bis(4-(carbazol-9-yl)phenyl)biphenyl,
2,8-bis(diphenylphosphoryl)dibenzo[b,d]thiophene,
bis(2-methylphenyl)diphenylsilane,
bis[3,5-di(9H-carbazol-9-yl)phenyl]diphenylsilane,
3,6-bis(carbazol-9-yl)-9-(2-ethylhexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole.

The emissive layer may be formed by co-deposition of any of these materials with a light-emitting dopant.

Specific examples of light-emitting dopants include
3-(2-benzothiazolyl)-7-(diethylamino)coumarin,
2,3,6,7-tetrahydro-1,1,7,7-tetramethyl-1H,5H,11H-10-(2-benzothiazolyl)quinolidino[9,9a,1gh]coumarin,
quinacridone, N,N'-dimethylquinacridone,
tris(2-phenylpyridine) iridium(III) (Ir(ppy)$_3$),
bis(2-phenylpyridine)(acetylacetonate) iridium(III) (Ir(ppy)$_2$(acac)),
tris[2-(p-tolyl)pyridine] iridium(III) (Ir(mppy)$_3$),
9,10-bis[N,N-di(p-tolyl)amino]anthracene,
9,10-bis[phenyl(m-tolyl)amino]anthracene,
bis[2-(2-hydroxyphenyl)benzothiazolate] zinc(II),
$N^{10},N^{10},N^{10'},N^{10'}$-tetra(p-tolyl)-9,9'-bianthracene-10,10'-diamine,
$N^{10},N^{10},N^{10'},N^{10'}$-tetraphenyl-9,9'-bianthracene-10,10'-diamine,
$N^{10},N^{10'}$-diphenyl-$N^{10},N^{10'}$-dinaphthalenyl-9,9'-bianthracene-10,10'-diamine,
4,4'-bis(9-ethyl-3-carbazovinylene)-1,1'-biphenyl,
perylene, 2,5,8,11-tetra-t-butylperylene,
1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis(3,5-difluoro)-2-(2-pyridyl)phenyl-(2-carboxypyridyl) iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)tris(9,9-dimethyl-fluorenylene),
2,7-bis{2-[phenyl(m-tolyl)amino]-9,9-dimethylfluoren-7-yl}-9,9-dimethylfluorene,
N-(4-((E)-2-(6((E)-4-(diphenylamino)styryl)naphthalen-2-yl)-vinyl)phenyl)-N-phenylbenzenamine,
fac-iridium(III) tris(1-phenyl-3-methylbenzimidazolin-2-ylidene-C,C$^{2'}$),
mer-iridium(III) tris(1-phenyl-3-methylbenzimidazolin-2-ylidene-C,C$^{2'}$),
2,7-bis[4-(diphenylamino)styryl]-9,9-spirobifluorene,
6-methyl-2-(4-(9-(4-(6-methylbenzo[d]thiazol-2-yl)phenyl)-anthracen-10-yl)phenyl)benzo[d]thiazole,
1,4-di[4-(N,N-diphenyl)amino]styrylbenzene,
1,4-bis(4-(9H-carbazol-9-yl)styryl)benzene,
(E)-6-(4-(diphenylamino)styryl)-N,N-diphenylnaphthalen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate) iridium(III),
bis(3-trifluoromethyl-5-(2-pyridyl)pyrazolate)(benzyl-diphenylphosphinate) iridium(III),
bis(1-(2,4-difluorobenzyl)-3-methylbenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyridinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinolin-2(1H)-ylidene)quinoline-2-amine-BF$_2$, (E)-2-(2-(4-(dimethylamino)styryl)-6-methyl-4H-pyran-4-ylidene)malononitrile,
4-(dicyanomethylene)-2-methyl-6-julolidyl-9-enyl-4-H-pyran,
4-(dicyanomethylene)-2-methyl-6-(1,1,7,7-tetramethyl-julolidyl-9-enyl)-4H-pyran,
4-(dicyanomethylene)-2-t-butyl-6-(1,1,7,7-tetramethyl-julolidin-4-ylvinyl)-4H-pyran,
tris(dibenzoylmethane)phenanthroline europium(III),
5,6,11,12-tetraphenylnaphthacene,
bis(2-benzo[b]thiophen-2-yl-pyridine)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline](acetylacetonate) iridium(III),
bis[2-(9,9-dimethyl-9H-fluoren-2-yl)quinoline](acetyl-acetonate) iridium(III),
tris[4,4'-di-t-butyl-(2,2')-bipyridine] ruthenium(III).bis(hexafluorophosphate),
tris(2-phenylquinoline) iridium(III),
bis(2-phenylquinoline)(acetylacetonate) iridium(III),
2,8-di-t-butyl-5,11-bis(4-t-butylphenyl)-6,12-diphenyltet-racene,
bis(2-phenylbenzothiazolate)(acetylacetonate) iridium(III),
platinum 5,10,15,20-tetraphenyltetrabenzoporphyrin,
osmium(II) bis(3-trifluoromethyl-5-(2-pyridine)pyrazolate)-dimethylphenylphosphine,
osmium(II) bis(3-trifluoromethyl)-5-(4-t-butylpyridyl)-1,2,4-triazolate)diphenylmethylphosphine,
osmium(II) bis(3-(trifluoromethyl)-5-(2-pyridyl)-1,2,4-triazole)dimethylphenylphosphine,
osmium(II) bis(3-(trifluoromethyl)-5-(4-t-butylpyridyl)-1,2,4-triazolate)dimethylphenylphosphine,
bis[2-(4-n-hexylphenyl)quinoline](acetylacetonate) iridium (III),
tris[2-(4-n-hexylphenyl)quinoline] iridium(III),
tris[2-phenyl-4-methylquinoline] iridium(III),
bis(2-phenylquinoline)(2-(3-methylphenyl)pyridinate) iridium(III),
bis(2-(9,9-diethylfluoren-2-yl)-1-phenyl-1H-benzo[d]-imidazolato)(acetylacetonate)
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III),
bis(phenylisoquinoline)(2,2,6,6-tetramethylheptane-3,5-dionate) iridium(III),
iridium(III) bis(4-phenylthieno[3,2-c]pyridinato-N,C$^{2'}$)-acetylacetonate,
(E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)-malononitrile,
bis(3-trifluoromethyl-5-(1-isoquinolyl)pyrazolate)(methyldiphenylphosphine) ruthenium,
bis[(4-n-hexylphenyl)isoquinoline](acetylacetonate) iridium(III),
platinum(II) octaethylporphin,
bis(2-methyldibenzo[f,h]quinoxaline)(acetylacetonate) iridium(III) and
tris[(4-n-hexylphenyl)isoquinoline] iridium(III).

Specific examples of electron transport layer/hole blocking layer-forming materials include
lithium 8-hydroxyquinolinate,
2,2',2''-(1,3,5-benzenetriyl)-tris(1-phenyl-1-H-benzimidazole),
2-(4-biphenyl)-5-(4-t-butylphenyl)-1,3,4-oxadiazole,
2,9-dimethyl-4,7-diphenyl-1,10-phenanthroline,
4,7-diphenyl-1,10-phenanthroline,
bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-t-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-t-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo-[4,5f][1,10]phenanthroline,
2-(naphthalen-2-yl)-4,7-diphenyl-1,10-phenanthroline,
phenyldipyrenylphosphine oxide,
3,3',5,5'-tetra[(m-pyridyl)phen-3-yl]biphenyl,
1,3,5-tris[(3-pyridyl)phen-3-yl]benzene,
4,4'-bis(4,6-diphenyl-1,3,5-triazin-2-yl)biphenyl,
1,3-bis[3,5-di(pyridin-3-yl)phenyl]benzene,
bis(10-hydroxybenzo[h]quinolinato)beryllium,
diphenylbis(4-(pyridin-3-yl)phenyl)silane and
3,5-di(pyren-1-yl)pyridine.

Examples of electron injection layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), lithium acetate and lithium benzoate.

Examples of cathode materials include aluminum, magnesium-silver alloys, aluminum-lithium alloys, lithium, sodium, potassium and cesium.

An example of an electron blocking layer-forming material is tris(phenylpyrazole)iridium.

The fabrication of polymer LED (PLED) devices using the charge-transporting varnish of the invention, although not particularly limited, is exemplified by the following method.

A PLED device having a charge-transporting thin-film formed using the charge-transporting varnish of the invention can be fabricated by, in the production of an OLED device as described above, successively forming a hole-transporting polymer layer and a light-emitting polymer layer instead of carrying out vacuum deposition operations for a hole transport layer, an emissive layer, an electron transport layer and an electron injection layer.

Specifically, the charge-transporting varnish of the invention is coated onto an anode substrate and a hole injection layer is formed by the above-described method. A hole-transporting polymer layer and a light-emitting polymer layer are then successively formed thereon, following which a cathode is vapor-deposited on top, thereby forming the PLED device.

The cathode and anode materials used here may be similar to those used when producing an OLED device as described above, and similar cleaning treatment and surface treatment may be carried out.

The method of forming the hole-transporting polymer layer and the light-emitting polymer layer is exemplified by a film-forming method in which a solvent is added to a hole-transporting polymer material or a light-emitting polymer material, or to the material obtained by adding to these a dopant substance, thereby dissolving or uniformly dispersing the material, following which the resulting solution or dispersion is coated onto the hole injection layer or hole-transporting polymer layer and subsequently baked.

Examples of hole-transporting polymer materials include
poly[(9,9-dihexylfluorenyl-2,7-diyl)-co-(N,N'-bis{p-butyl-phenyl}-1,4-diaminophenylene)],
poly[(9,9-dioctylfluorenyl-2,7-diyl)-co-(N,N'-bis{p-butyl-phenyl}-1,1'-biphenylene-4,4-diamine)],
poly[(9,9-bis(1,1'-penten-5'-yl)fluorenyl-2,7-diyl)-co-(N,N'-bis{p-butylphenyl}-1,4-diaminophenylene)],
poly[N,N'-bis(4-butylphenyl)-N,N'-bis(phenyl)benzidine] end-capped with polysilsesquloxane and
poly[(9,9-dioctylfluorenyl-2,7-diyl)-co-(4,4'-(N-(p-butyl-phenyl))diphenylamine)].

Examples of light-emitting polymer materials include polyfluorene derivatives such as poly(9,9-dialkylfluorene) (PDAF), poly(phenylene vinylene) derivatives such as poly(2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate, either within an inert gas atmosphere or in a vacuum.

In addition, given that not only charge-transporting thin-films obtained from the above-described charge-transporting varnishes, but also vapor-deposited films obtained from the aniline derivatives of the invention have excellent charge transportability, depending on the intended application, use can be made of a charge-transporting thin-film obtained by vapor deposition.

EXAMPLES

Production Examples and Working Examples are given below to more concretely illustrate the invention, although the invention is not limited by these Examples. The equipment used was as follows.

(1) $^1$H-NMR Measurement:
  JNM-ECP300 FT NMR System, from JEOL, Ltd.
(2) MALDI-TOF-MS:
  Autoflex III SmartBeam, from Bruker Daltonics
(3) Substrate Cleaning:
  Substrate cleaning machine (reduced-pressure plasma system), from Choshu Industry Co., Ltd.
(4) Varnish Coating:
  MS-A100 Spin Coater, from Mikasa Co., Ltd.
(5) Film Thickness Measurement:
  Surf corder ET-4000 microfigure measuring instrument, from Kosaka Laboratory, Ltd.
(6) EL Device Fabrication:
  C-E2L1G1-N Multifunction Vapor Deposition System, from Choshu Industry Co., Ltd.

(7) Measurement of EL Device Brightness:
  I-V-L Measurement System from Tech World, Inc.

[1] Compound Synthesis

[Production Example 1] Synthesis of Aniline Derivative 1

[Chemical Formula 13]

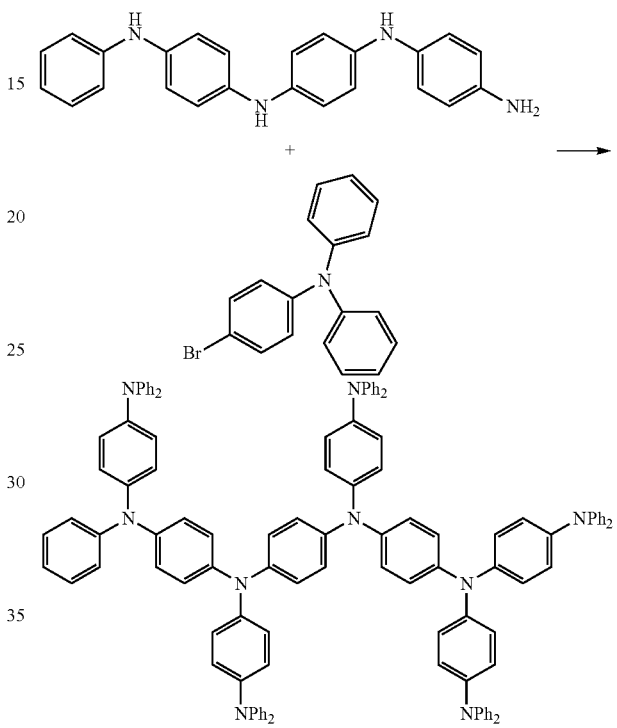

A reactor was charged with 1.50 g of tetraaniline, 6.92 g of 4-bromotriphenylamine, 118 mg of Pd(dba)$_2$ and 2.48 g of t-butoxysodium and the reactor was flushed with nitrogen, following which 35 mL of toluene and 1.4 mL of a toluene solution of tri-t-butylphosphine that was separately prepared beforehand (concentration, 59 g/L) were added and the mixture was stirred for 24 hours at 50° C. After the system cooled down to room temperature, toluene and saturated saline were added, and liquid-liquid separation was carried out. The organic layer was dried over anhydrous sodium sulfate, following which silica gel filtration was carried out. Next, 0.3 g of activated carbon was added to the resulting filtrate, and stirring was carried out for 1 hour at room temperature. The activated carbon was then removed by filtration and the filtrate was concentrated. The resulting concentrate was added dropwise to a mixed solvent consisting of 300 mL of ethyl acetate and 300 mL of methanol, and the slurry that formed was filtered. The resulting powder was dried, dissolved again in about 100 mL of 1,4-dioxane and the solution was added dropwise to 500 mL of methanol. The slurry that formed was filtered, and the resulting powder was dried, giving the target Aniline Derivative 1 (4.90 g; yield, 76%).

$^1$H-NMR (300 MHz, THF-d8) δ [ppm]: 7.17-7.22 (m, 20H), 6.90-7.06 (m, 57H).

MALDI-TOF-MS, m/Z; found: 1582.47 ([m]$^+$ calculated: 1581.71).

[2] Preparation of Charge-Transporting Varnish

Working Example 1

A charge-transporting varnish was prepared by dissolving 0.108 g of Aniline Derivative 1 as the charge-transporting substance, 0.202 g of phosphotungstic acid (PTA) as the dopant substance and 0.094 g of tetrafluorotetracyanoquinodimethane (F4TCNQ) in 14.0 g of 1,3-dimethyl-2-imidazolidinone (DMI), adding thereto 4.0 g of 2,3-butanediol and 2.0 g of propylene glycol monomethyl ether (PGME) and stirring, and then further adding 0.007 g of 3,3,3-trifluoropropyltrimethoxysilane (Shin-Etsu Chemical Co., Ltd.) and 0.013 g of phenyltrimethoxysilane (Shin-Etsu Chemical Co., Ltd.) and stirring.

[3] Fabrication of Organic EL Device and Evaluation of Device Characteristics

Working Example 2

The varnish obtained in Working Example 1 was coated onto an ITO substrate using a spin coater, then dried for 1 minute at 80° C. and subsequently baked for 5 minutes at 150° C. in an open-air atmosphere, thereby forming a uniform 30 nm thin-film on an ITO substrate. A glass substrate with dimensions of 25 mm×25 mm×0.7 mm (t) and having indium-tin oxide (ITO) patterned on the surface to a film thickness of 150 nm was used as the ITO substrate. Prior to use, impurities on the surface were removed with an O$_2$ plasma cleaning system (150 W, 30 seconds).

Next, using a vapor deposition system (degree of vacuum, 1.0×10$^{-5}$ Pa), α-NPD was deposited to a thickness of 30 nm at a rate of 0.2 nm/s onto the ITO substrate on which a thin-film had been formed. CBP and Ir(PPy)$_3$ were subsequently co-deposited. In co-deposition, the deposition rate was controlled so that the Ir(PPy)$_3$ concentration became 6%, and a 40 nm layer was formed. Thin-films of BAlq, lithium fluoride and aluminum were then successively deposited, thereby giving an organic EL device. At this time, vapor deposition was carried out at a rate of 0.2 nm/s for BAlq and aluminum, and at a rate of 0.02 nm/s for lithium fluoride. The film thicknesses were set to, respectively, 20 nm, 0.5 nm and 120 nm.

To prevent the device characteristics from deteriorating due to the influence of oxygen, moisture and the like in air, the organic EL device was sealed with sealing substrates, following which the characteristics were evaluated. Sealing was carried out by the following procedure. In a nitrogen atmosphere having an oxygen concentration of 2 ppm or less and a dew point of not more than −85° C., the organic EL device was placed between sealing substrates and the sealing substrates were laminated together using an adhesive (MORESCO Moisture Cut WB90US(P), from Moresco Corporation). At this time, a desiccant (HD-071010W-40, from Dynic Corporation) was placed, together with the organic EL device, within the sealing substrates. The laminated sealing substrates were irradiated with UV light (wavelength, 365 nm; dosage, 6,000 mJ/cm$^2$), and then annealed at 80° C. for 1 hour to cure the adhesive.

The driving voltage, brightness and luminous efficiency at a driving current of 0.7 mA were measured for the fabricated device. The results are shown in Table 1. The size of the light-emitting surface in each device was 2 mm×2 mm.

TABLE 1

| | Voltage (V) | Brightness (cd/m$^2$) | Emission efficiency (cd/A) |
|---|---|---|---|
| Working Example 2 | 9.29 | 4,979 | 28.5 |

As shown in Table 1, an organic EL device having, as the hole injection layer, a charge-transporting thin-film obtained from a charge-transporting varnish of the invention exhibits excellent brightness characteristics.

The invention claimed is:

1. An aniline compound characterized by having formula (1)

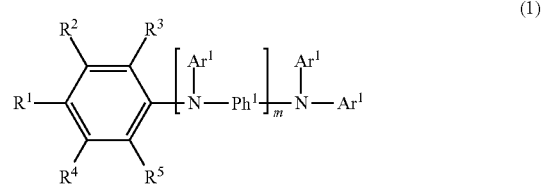

(1)

wherein R$^1$ to R$^5$ are each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom;

each Ph$^1$ is independently a group of formula (P1)

(P1)

(R$^6$ to R$^9$ being each independently a hydrogen atom, a halogen atom, a nitro group, a cyano group, or an alkyl group of 1 to 20 carbon atoms, alkenyl group of 2 to 20 carbon atoms, alkynyl group of 2 to 20 carbon atoms, aryl group of 6 to 20 carbon atoms or heteroaryl group of 2 to 20 carbon atoms which may be substituted with a halogen atom);

each Ar$^1$ is independently a group having any of formulas (A1) to (A14);

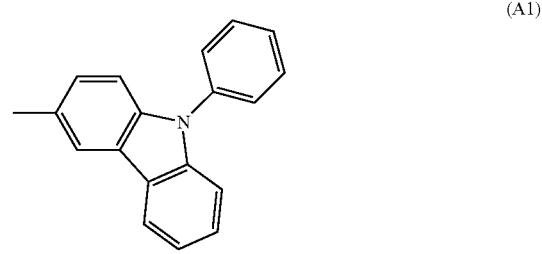

(A1)

(A2) 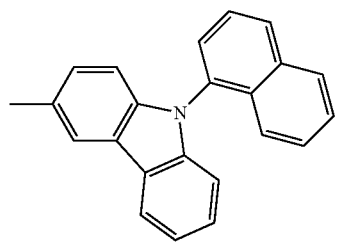
(A3) 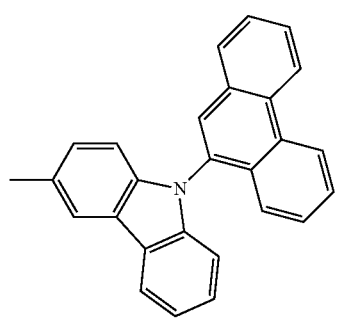
(A4) 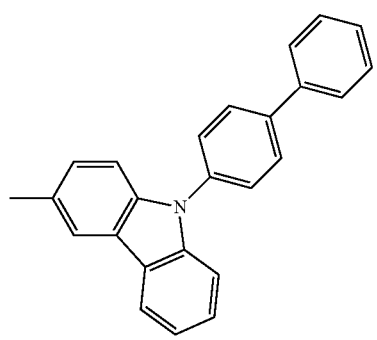
(A5) 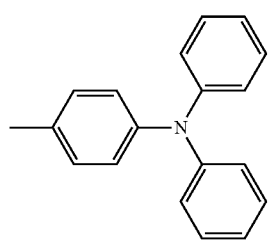
(A6) 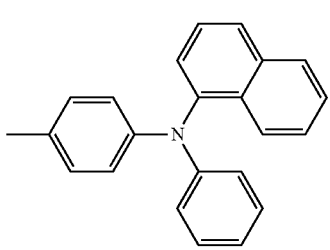
(A7) 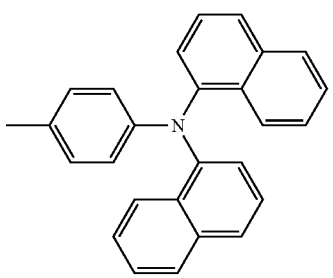
(A8) 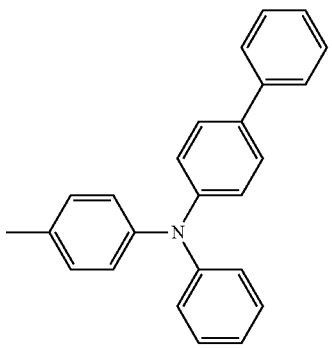
(A9) 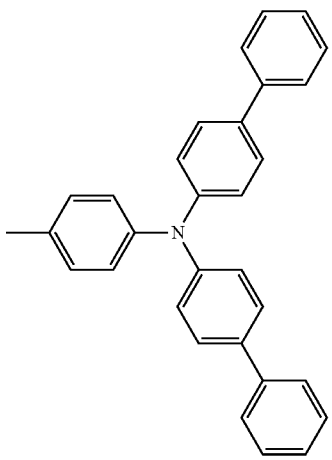
(A10) 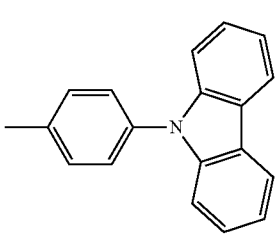
(A11) 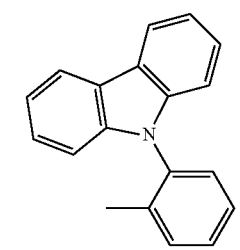

-continued

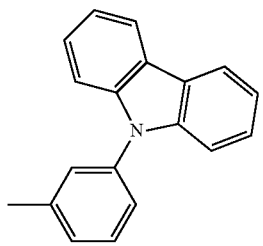
(A12)

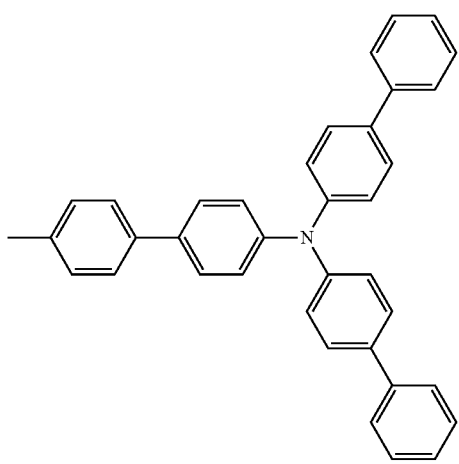
(A13)

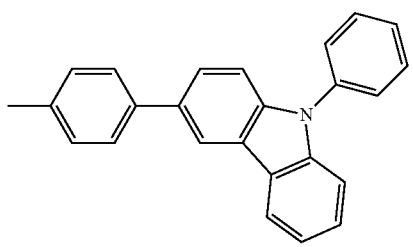
(A14)

and m is an integer from 3 to 5.

2. The aniline compound of claim 1, wherein $R^1$ to $R^9$ are all hydrogen atoms.

3. The aniline compound of claim 1, wherein each $Ar^1$ is independently a group having any of formulas (A1) to (A12).

4. The aniline compound of claim 3, wherein each $Ar^1$ is independently a group having any of formulas (A1) to (A3), (A5) to (A7) and (A10) to (A12).

5. The aniline compound of claim 1, wherein the $Ar^1$ moieties are all identical groups.

6. A charge-transporting substance consisting of the aniline compound of claim 1.

7. A charge-transporting material comprising the charge-transporting substance of claim 6.

8. A charge-transporting varnish comprising the charge-transporting substance of claim 6 and an organic solvent.

9. The charge-transporting varnish of claim 8 which further comprises a dopant substance.

10. The charge-transporting varnish of claim 9, wherein the dopant substance comprises a halotetracyanoquinodimethane compound.

11. The charge-transporting varnish of claim 10, wherein the dopant substance further comprises a heteropolyacid.

12. A charge-transporting thin-film produced using the charge-transporting varnish of claim 8.

13. An electronic device comprising the charge-transporting thin-film of claim 12.

14. An organic electroluminescent device comprising the charge-transporting thin-film of claim 12.

15. A method of producing a charge-transporting thin-film, which method is characterized by comprising the step of coating a substrate with the charge-transporting varnish of claim 8 and evaporating off the solvent.

16. A method of preparing the aniline compound of claim 1, which method is characterized by comprising the step of reacting an amine compound of formula (2)

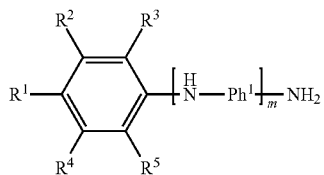
(2)

(wherein $R^1$ to $R^5$, $Ph^1$ and m are as defined above) with an aryl compound of formula (3)

$$Ar^1-Z \qquad (3)$$

(wherein Z is a halogen atom or a pseudo-halogen group, and $Ar^1$ is as defined above) in the presence of a catalyst.

* * * * *